United States Patent [19]

Schleicher et al.

[11] 4,186,738
[45] Feb. 5, 1980

[54] HEEL SUPPORTING BOOT FOR BED PATIENTS

[76] Inventors: Thomas R. Schleicher, 1819 Oak St., Northbrook, Ill. 60062; Donald J. Maylahn, 4255 Madison St., Skokie, Ill. 60076; Denis B. Drennan, 4 Milburn Park, Evanston, Ill. 60201

[21] Appl. No.: 877,876

[22] Filed: Feb. 15, 1978

[51] Int. Cl.² ............................................. A61F 5/30
[52] U.S. Cl. ................................. 128/153; 128/80 R
[58] Field of Search .................. 128/149, 153, 132 R, 128/165, 80 R

[56] References Cited

U.S. PATENT DOCUMENTS

| 3,606,884 | 9/1971 | Peter | 128/80 R |
|---|---|---|---|
| 3,693,619 | 9/1972 | Williams | 128/153 X |
| 4,076,022 | 2/1978 | Walker | 128/149 |

Primary Examiner—John D. Yasko
Attorney, Agent, or Firm—Mason, Kolehmainen, Rathburn & Wyss

[57] ABSTRACT

A heel supporting and protective boot for bed patients comprises a body formed of flexible, resilient, open-celled, nonallergenic, sheet-like, foam material having an inside supporting surface provided with a plurality of alternate peaks and valleys, with the peaks adapted for contact against the skin of the patient. The body includes a pair of opposite sidewall portions adapted to bear against and support the sides of the patient's lower leg, ankle and foot. A leg support portion is provided between the opposite sidewall portions for supporting the patient's leg with the heel at a level above the adjacent bed surface and well exposed to the air, generally out of contact with adjoining portions of the boot. The body of the boot also includes a foot support portion for supporting the sole of the patient's foot in an upright position and without contact with the patient's heel. Fastening means is provided for securely interconnecting the opposite sidewall portions above the patient's leg for positively retaining the boot in place in a secure manner.

25 Claims, 4 Drawing Figures

HEEL SUPPORTING BOOT FOR BED PATIENTS

BACKGROUND OF THE INVENTION

1. Field of the Invention

The present invention is directed towards a new and improved heel supporting and protecting boot for bed patients and more particularly to a heel supporting boot especially designed for preventing and aiding in the cure of decubitus ulcers of the heel in bed patients.

2. Description of the Prior Art

A number of devices have been developed for supporting and protecting the feet, heels and elbows of bed patients such as the cushion protector of U.S. Pat. No. 3,693,619, the foot protector of U.S. Pat. No. 3,511,233, the protective shields for bed patients of U.S. Pat. No. 3,216,417 and the foot board of U.S. Pat. No. 2,986,747. Existing prior art devices have been subject to a number of difficulties and disadvantages including the tendency to come loose, fall off or become disengaged from the patient as a result of patient movement and activity. In addition, many prior art devices do not positively relieve and reduce pressure and friction between the heel or joint of the patient and the bed sheet. In addition, many devices are hot and uncomfortable to wear and cause a build up of high temperatures because of the lack of adequate air ventilation. These conditions enhance the formation of decubitus ulcers. In addition, many prior art products actually create high pressure contact points against the patient's body at which points sores often develop. In addition, many devices are cumbersome, hot and unconfortable to wear.

SUMMARY OF THE INVENTION

It is an object of the present invention to provide a new and improved heel or joint supporting boot for bed patients which eliminates all or many of the disadvantages and problems encountered with prior art devices.

It is another object of the present invention to provide a new and improved heel supporting boot of the character described which is especially useful in the prevention and cure of decubitus ulcers of the heel.

Another object of the present invention is to provide a new and improved heel supporting boot which eliminates friction and pressure contact between the patient's heel and the bed sheet or bed covers.

Yet another object of the invention is to provide a new and improved heel supporting boot for bed patients wherein the heel is supported in a manner substantially fully exposed to the atmosphere.

Yet another object of the present invention is to provide a new and improved heel supporting boot which provides support for the sole of a patient's foot and is useful in preventing foot drop.

Yet another object of the present invention is to provide a new and improved heel supporting boot of the character described which provides better air ventilation around the patient's foot and leg and greatly reduces the possibility of heat build up and the resultant discomfort thereof.

Yet another object of the present invention is to provide a new and improved joint supporting device of the character described which is easy to put on and take off and yet which is not easily, dislodged, detached or kicked off by a patient's movement and activity.

Yet another object of the present invention is to provide a new and improved heel supporting boot which eliminates areas of high pressure contact and friction between the surface of the patient's skin and the inside surfaces of the boot.

Another object of the present invention is to provide a new and improved heel supporting boot having a novel fastening system for attaching and securely retaining the boot in a proper supportive position on a patient's limb.

Yet another object of the present invention is to provide a new and improved heel supporting boot which is suitable for use by patients of different size and weight.

Yet another object of the present invention is to provide a new and improved heel supporting boot which is worn in bed and may also be worn while the patient is ambulatory or in a wheel chair.

Yet another object of the present invention is to provide a new and improved heel suspension boot of the character described which provides for increased air circulation around the patient's limb.

Yet another object of the present invention is to provide a new and improved heel supporting boot which is light in weight, easy to put on and take off, and economical of manufacture.

Yet another object of the invention is to provide a new and improved heel supporting boot which provides lateral support for the foot on opposite sides.

The foregoing and other objects and advantages of the present invention are accomplished in an illustrated embodiment by way of representation and not limitation, which embodiment comprises a new and improved heel supporting boot for bed patients and the like having a body of flexible, resilient, sheet-like, compressible, open-celled, nonallergenic foam material. The flexible foam material has a convoluted, inside support surface with a plurality of alternate peaks and valleys and the peaks are adapted for supportive contact against the skin of a patient. The body includes a pair of sidewall portions adapted to bear against opposite sides of a patient's lower leg and foot and a leg support portion extends transversely between the sidewall portions supporting the patient's leg with the heel spaced well above and out of contact with the adjacent bed surface, bed sheet or blanket. This support is provided on the patient's leg, remote and upwardly away from the patient's heel so that the heel itself is almost entirely exposed to the atmosphere. In addition, the open-celled foam material "breathes" and air circulates through the valleys in the foam material adjacent the patient's skin. The body also includes a transversely extending foot support for engagement with the upper portion of the sole of the reclining patient's foot which is supported and held in an upright position. A lower edge of the foot support terminates at a level above the patient's heel and is out of contact therewith so that the heel is well exposed to the air, yet "foot drop" is prevented. A novel fastening system is provided for interconnecting opposite sidewalls above the patient's leg in a manner whereby the boot is positively retained in place on the patient's leg even though substantial patient movement and activity may occur.

BRIEF DESCRIPTION OF THE DRAWINGS

For a better understanding of the invention, reference should be had to the following detailed description taken in conjunction with the drawings, in which.

DESCRIPTION OF THE PREFERRED EMBODIMENT

Figure 2:
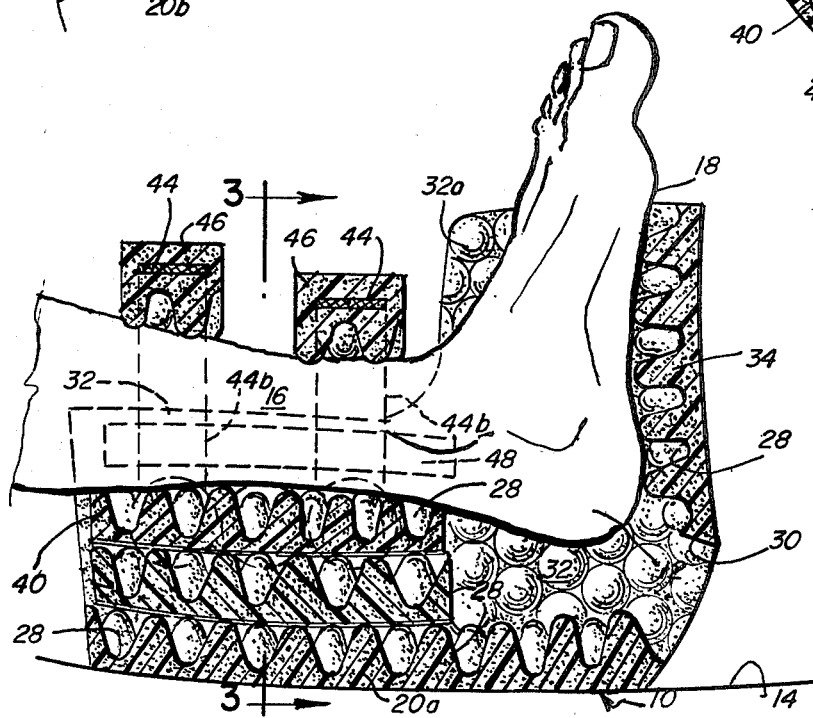
FIG. 2 is a longitudinal sectional view taken substantially along lines 2—2 of FIG. 1.

Referring now more particularly to the drawings, therein is illustrated a new and improved heel supporting and protective boot for bed patients and the like, referred to generally by the reference numeral 10 and constructed in accordance with the features of the present invention. As best illustrated in FIG. 2, the boot 10 is designed to support and elevate the heel 12 of a bed patient so that the skin of the heel does not come in contact with the surface of the bed such as a blanket or sheet represented by the numeral 14. In addition, the heel supporting boot provides support for the patient's leg 16 over a relatively large area which is remote from and proximal to the patient's heel 12. The boot also provides support for the sole 18 of the patient's foot at a position away from the heel and this prevents and retards a malady known as "foot drop" which occurs in bed patients confined to the reclining position for periods of time.

Figure 4:
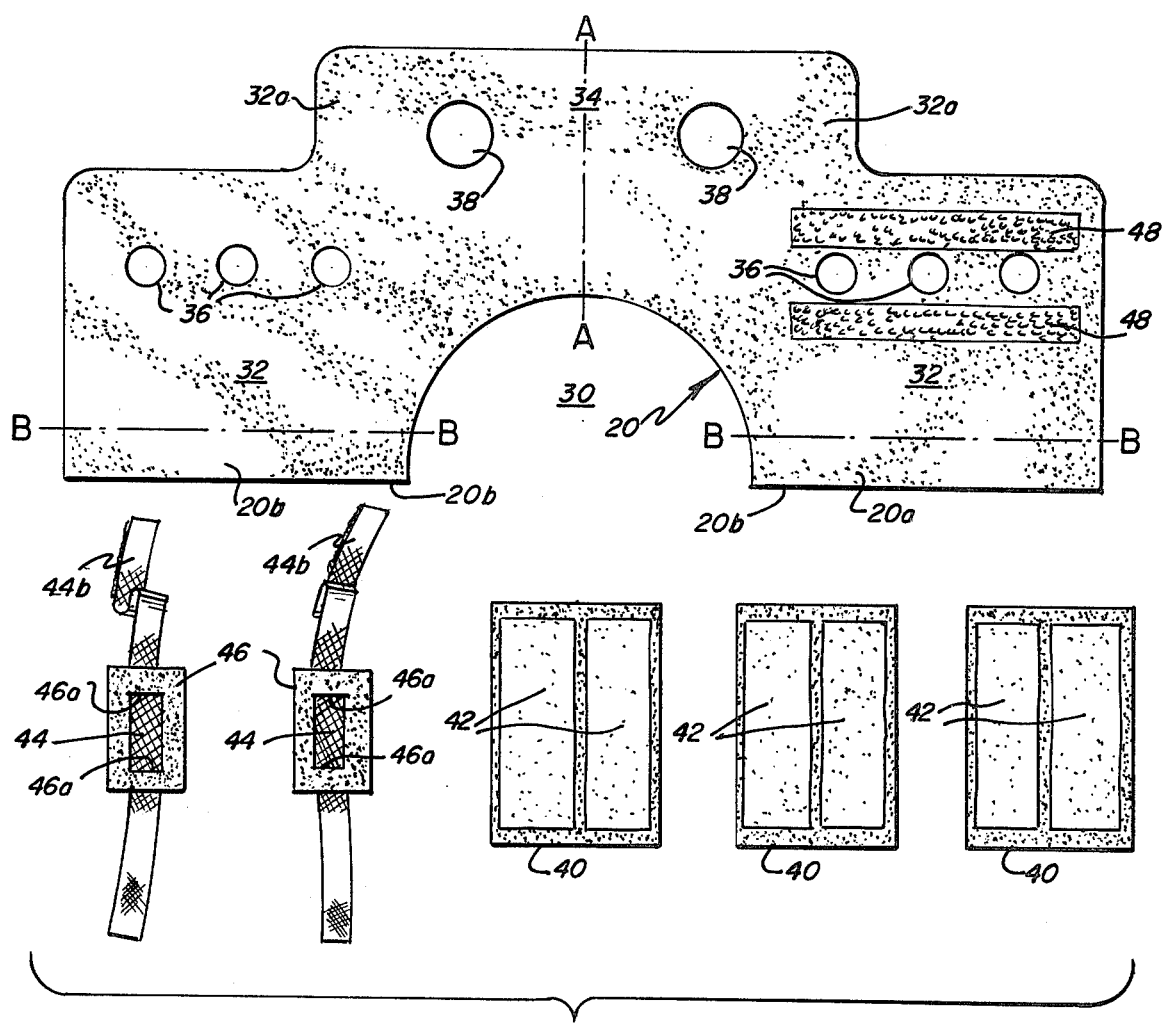
FIG. 4 is an exploded view illustrating the components and a pattern of the foam material that is utilized for constructing the novel heel supporting boot.
Figure 5:
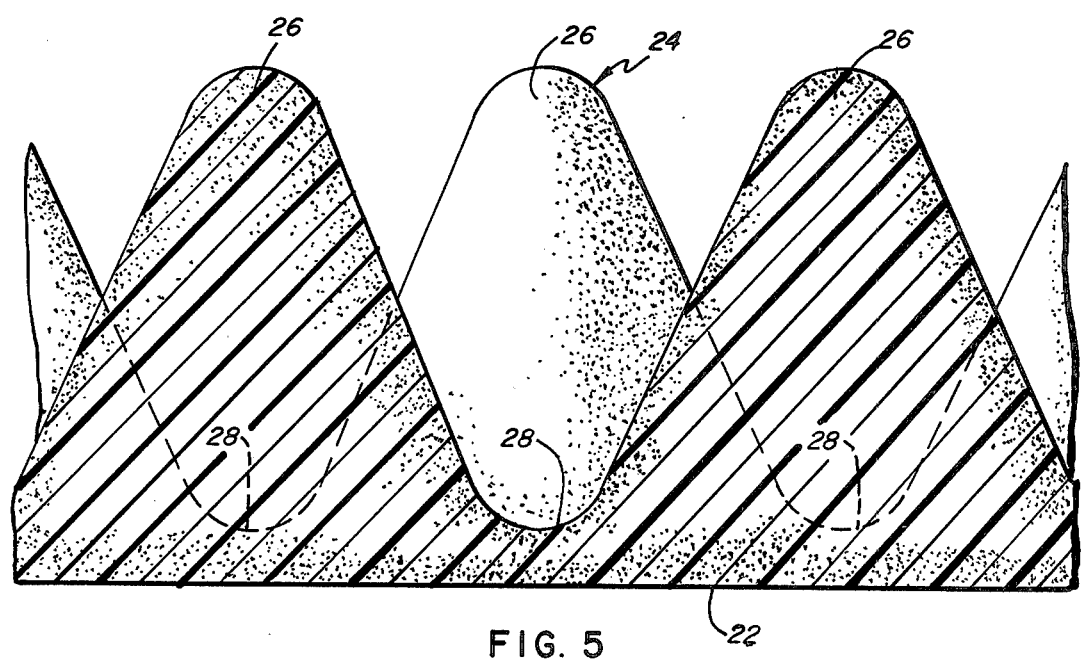
FIG. 5 is a fragmentary, enlarged, cross-sectional view illustrating in detail the profile of the flexible, resilient, sheet-like, foam material in accordance with the present invention.

In accordance with the present invention, the heel protecting boot 10 includes a body initially formed from a flat, unitary piece of flexible, resilient, open-celled, nonallergenic, sheet-like, cellular foam material cut in a pattern-like shape or profile shown in FIG. 4. The foam material itself is shown in enlarged, cross-sectional detail in FIG. 5, and includes a relatively smooth, flat outer surface or skin 22 and a convoluted inside skin surface 24 adapted for contact with the skin of the patient and formed with an undulating surface pattern of alternate peaks 26 and valleys 28. In forming the boot, the body 20 is initially cut or stamped out of a flat sheet of the foam material and is then folded about a vertical axis represented by the line A—A. Lower wall portions 20a are then folded inwardly about the axes represented by the lines B—B and outer edges are then joined together by stitching or other adhesive means along a joint line 20b to form a seam which runs longitudinally of the boot along the bottom wall. Because the cellular foam material of the boot is resilient and compressible when the peaks 26 are pressed into contact against the patient's skin, the peaks flatten out to distribute the pressure over larger areas, however, the relatively deep valleys 28 still provide a large area of circulating air passages around the skin surface and these passages permit air to flow in and around the skin. The open-celled foam material also "breathes" over the relatively large area of contact between the peaks 26 on the convoluted inside surface 24 and the patient's skin. In accordance with the invention, a relatively large, heel ventilating opening or hole 30 is formed at the intersection of the axes A—A and B—B to permit air circulation around the exposed heel 12 and into and out of the various passages adjacent the patient's skin formed by the valleys 28.

In accordance with the present invention, the boot 10 is provided with a pair of longitudinal, laterally opposite sidewall portions 32 which are somewhat L-shaped in elevation with upwardly extending toe portions 32a adjacent the foot end of the boot. The sidewall portions are integral with the folded under bottom wall portions 20a which extend inwardly below and support the leg of the patient and which are joined together longitudinally along the seam 20b as previously described. At the toe of the foot end, the sidewall portions are integral with a transversely extending foot support wall 34 which provides support for the sole of the foot upwardly above the heel. This foot support is integral with the upstanding toe end portions 32a of the sidewall portions. Each sidewall portion is provided with a plurality of ventilating openings 36 aligned in a row longitudinally of the boot and the boot is also provided with a pair of larger, toe end, ventilating openings 38 adjacent an upper level on the upstanding toe end wall portions 32a. This group of large ventilating openings provide for excellent air circulation around the inside surface 24 of the boot adjacent the surface of the patient's skin.

In order to positively support the patient's leg 16 so that the heel 12 is out of frictional, pressurized contact with any interior surfaces 24 of the boot, there is provided one or more leg support cushions 40 of generally rectangular shape and also formed of the same sheet type foam material as the boot body. The leg support cushions may be stacked one on top of the other as shown between the opposite sidewall portions 32 and are positioned in the bottom wall sections 20a and remotely away from the lower heel 12. With large or heavy patients, two or three cushions may be provided to better insure that the patient's heel 12 is elevated out of contact with the inside surface 24 of the boot whereas with small or lighter patients, only a single cushion may be required. One size of boot is thus able to accommodate a wide range in patient size and weight. In order to secure the leg support cushions 40 to each other in a stack and to secure the lowest cushion on the supporting bottom wall sections 20a of the boot, the bottom or smooth surface of each cushion is provided with a pair of adhesive strips 42 having adhesive material on both sides and a removable, peel-off, cover which is removed when ready for use to expose the adhesive material for adhesive holding engagement with another cushion or with the bottom leg supporting wall segments 20a of the boot.

Figure 1:
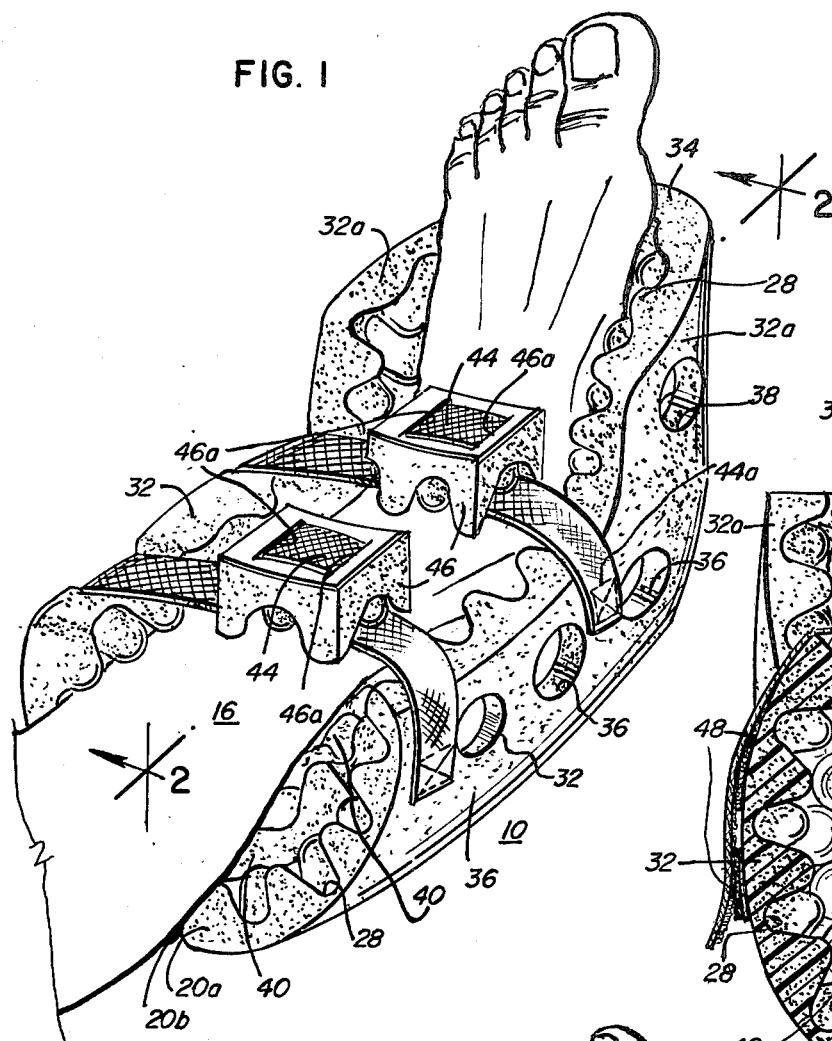
FIG. 1 is a perspective, elevational view illustrating a new and improved heel protecting boot constructed in accordance with the features of the present invention and shown as it is worn by a bed patient.
Figure 3:
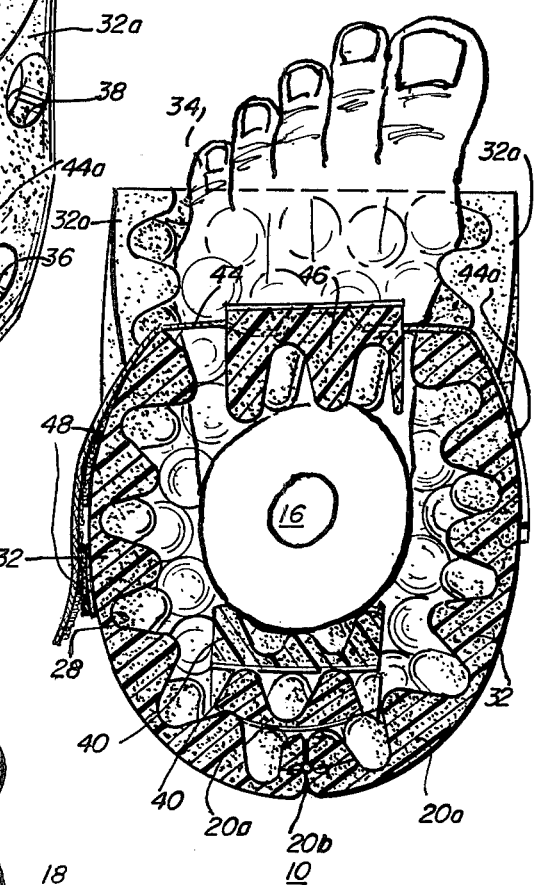
FIG. 3 is a transverse, cross-sectional view taken substantially along lines 3—3 of FIG. 2.

In accordance with the present invention, the heel protecting boot 10 is provided with a novel fastening system for positively securing the boot in place on the leg and foot of a bed patient. The fastening system includes a pair of longitudinally, spaced apart, transversely, extending, flexible straps 44 attached to one of the sidewall portions 32 at longitudinally spaced apart positions by stitching 44a. Intermediate the ends, the fastening straps 44 are provided with leg cushion pads 46 formed of the same type foam material used for the body of the boot and these cushion pads are provided with slits 46a so that the straps 44 are readily threaded or passed therethrough and so that the pads may be thereafter adjusted in position longitudinally on the straps as best shown in FIGS. 1 and 2. The upper leg cushion pads 46 prevent areas of high contact pressure between the straps 44 and the skin of the patient which might cause chaffing and sores, yet the pads provide a firm and secure holding force on the patient's leg to support the boot at longitudinally spaced apart positions. At the free outer end portion 44b of each strap, there is provided on the underside, a detachable fastening area formed of a plurality of small filamentary hooking and loop elements of the type produced and sold by Velcro S.A., Soulie, Nyon, Switzerland. These type of fastening elements are shown and described in U.S. Pat. No. 3,748,701. A pair of cooperating flexible, fastener straps 48 with a plurality of small filamentary hooking and loop elements on the outer surface are provided on opposite sides of the row of openings 26 on the opposite sidewall portion 32, as best shown in FIG. 4. The hook and loop type fastening elements on the cooperating transverse strap portions 44b and the longitudinal strips 48 provide a positive holding but readily detachable system which facilitates the putting on and taking off the heel protective boot when desired. The fastening system provides excellent protection against the boot being kicked off during the night because of patient movements. The transverse straps are spaced at longitudinal intervals on the boot and extend over the patient's leg and the fastener strips 48 on the boot sidewall portion 32 are generally transverse thereto so that four areas or regions of criss-crossing attachment are provided between the plurality of small hook-like filamentary fastening elements on the respective straps and strips. This arrangement has proved far superior to the customary types of cloth ties, tapes, bands and the like.

From the foregoing, it will be seen that the heel protecting boot 10 provides support for the heel 12 of a bed patient in a manner whereby the heel itself is positively maintained out of high pressure and frictional contact with a bed surface 14 or the adjacent inside surface 24 of the boot wall itself. A relatively large, heel ventilating opening 30 plus the openings 26 and 28 provide for good air circulation around the heel and foot. The resilient foam material of the boot body 20 provides a plurality of air ventilating passages in the valleys 28 of the inside surface 24 around and between the spaced apart peaks 26. The compressible, resilient, open-celled, foam material provides leg and foot support over a spread out, relatively large area of the skin surface so that friction and contact pressure is reduced and the chances of bed sores are minimized. The foot support portion 34 prevents a malady of "foot drop" and the novel fastening system positively retains the boot 10 in place yet permits the easy and rapid removal of the boot when desired.

The open cellular foam material enables the boot walls to breathe and thus provides additional air ventilation along with the large number of diverse passages formed by the valleys 28 and the ventilating openings 36, 38 and 30. The boot can be worn for extended periods with minimal heat build up and is unusually comfortable for a device of this character. The boot will accommodate patients in a wide range of sizes and weights and is relatively economical to produce in a relatively large quantity.

The boot is particularly effective in preventing decubitus ulcers of the heel from developing and provides a means for aiding in the treatment of ulcers that have developed. The upper foot portions 32a of the opposite sidewall portions 32 provide lateral support for the opposite sides of the patient's foot when appropriate and the fastening system straps 44 can be loosely secured as desired to permit some freedom of movement between the sidewall portions of the boot.

Although the present invention has been described with reference to a single illustrated embodiment thereof, it should be understood that numerous other modifications and embodiments can be devised by those skilled in the art that will fall within the spirit and scope of the principles of this invention.

What is claimed as new and desired to be secured by Letters Patent of the United States is:

1. A heel supporting boot for bed patients comprising:

a body formed of flexible, resilient, sheet foam material having an inside support surface provided with a plurality of alternate peaks and valleys with the peaks adapted for contact against the skin of the patient, said body including a pair of sidewall portions adapted to bear against opposite sides of a patient's lower leg and ankle, a leg support portion between said sidewall portions, and a foot portion for supporting the sole of the patient's foot in an upright condition remotely away from the patient's heel, said foot portion extending above the upper level of said sidewall portions adjacent said patient's leg;

at lease one leg support cushion formed of said foam material securable on said leg support portion between said sidewall portions spaced from the patient's heel for supporting the patient's leg with the heel in an elevated position above an adjacent bed surface out of contact with said leg support portion of said body, and detachable fastening means for interconnecting said sidewall portions above said patient's leg to retain said boot in place on the patient's leg.

2. The heel supporting boot of claim 1 wherein said body is formed of a single piece of said sheet material with an enlarged opening adjacent the patient's heel.

3. The heel supporting boot of claim 1 wherein said body is formed with a plurality of ventilating openings therein.

4. The heel supporting boot of claim 1 wherein said foot portion and sidewall portions are formed of a continuous piece of said sheet material.

5. The heel supporting boot of claim 2 wherein said heel opening is formed between a lower edge of said foot support and an edge of said leg support.

6. The heel supporting boot of claim 5 wherein edges of said single piece of sheet material are joined along a seam positioned to extend longitudinally of said heel opening.

7. The heel supporting boot of claim 6 wherein said seam is formed in said leg support between said sidewall portions.

8. The heel supporting boot of claim 1 wherein said detachable fastening means includes a pair of elongated flexible webs having faces thereon provided with a plurality of small filamentary detachable, hooking elements, one of said webs adapted to extend transversely over the patient's leg and fixedly secured to one of said sidewall portions of said body.

9. The heel supporting boot of claim 8 wherein the other of said webs is mounted longitudinally along the other of said sidewall portion for detachable connection with said one web generally transverse thereto.

10. The heel supporting boot of claim 8 wherein said fastening means includes a plurality of said one webs spaced longitudinally apart along said sidewall portions.

11. The heel supporting boot of claim 9 wherein said fastening means includes a plurality of said other webs generally parallel of each other longitudinally mounted on a side portion of said body for detachable connection with one or more of said one webs.

12. The heel supporting boot of claim 8 including pad means of said sheet foam material secured on said one web for contact against an upper surface of the patient's leg.

13. The heel supporting boot of claim 8 wherein at least one of said sidewall portions of said body is provided with one or more ventilating openings.

14. The heel supporting boot of claim 13 wherein at least one of said sidewall portions of said body is formed with a plurality of longitudinally spaced apart ventilating openings and including one or more closure straps attached to a portion of said boot below said openings.

15. The heel supporting boot of claim 14 wherein said ventilating openings are aligned in a row and including a plurality of said other webs on opposite sides of said row for detachable connection with one or more of said one webs generally transverse thereto.

16. The heel supporting boot of claim 15 including a plurality of said one webs secured at longitudinally spaced apart position on said one sidewall portion for detachable connection with said plurality of other webs on said other of said sidewall portions.

17. The heel supporting boot of claim 1 wherein said sidewall portions of said boot include upwardly extending end portions adjacent said foot support for supporting opposite sides of said patient's foot.

18. The heel supporting boot of claim 17 wherein said upwardly extending end portions on said sidewall portions are integral with opposite edges of said foot support.

19. The heel supporting boot of claim 1 including adhesive means for securing said leg support cushion on said leg support portion between said sidewall portions.

20. The heel supporting boot of claim 19 wherein said adhesive means includes a sheet of pressure sensitive adhesive material for contact between said leg support portion and said leg support cushion.

21. The heel supporting boot of claim 1 wherein said sheet material of said body includes a smooth flat outer surface.

22. The heel supporting boot of claim 1 wherein said sheet material comprises open celled foam.

23. The heel supporting boot of claim 22 wherein said sheet material comprises non-allergenic urethane foam.

24. The heel supporting boot of claim 1 including a plurality of said leg support cushions arranged in a stack, one on top of another, and at least an upper one in said stack removably attached to a next adjacent lower cushion in the stack for adjusting the amount of elevation of said patient's heel.

25. The heel supporting boot of claim 24 wherein said upper one of said cushions is adhesively secured to said next adjacent lower cushion in the stack.

* * * * *